United States Patent
Wang et al.

(10) Patent No.: US 7,233,710 B2
(45) Date of Patent: Jun. 19, 2007

(54) POLYMER BASED ELECTRO-OPTIC SCANNER FOR IMAGE ACQUISITION AND DISPLAY

(75) Inventors: Wei-Chih Wang, Sammamish, WA (US); Per G. Reinhall, Seattle, WA (US)

(73) Assignee: University of Washington, Seattle, WA (US)

( * ) Notice: Subject to any disclaimer, the term of this patent is extended or adjusted under 35 U.S.C. 154(b) by 66 days.

(21) Appl. No.: 11/068,939

(22) Filed: Feb. 28, 2005

(65) Prior Publication Data

US 2005/0238277 A1 Oct. 27, 2005

Related U.S. Application Data

(60) Provisional application No. 60/548,930, filed on Mar. 1, 2004.

(51) Int. Cl.
*G02F 1/335* (2006.01)
*G02F 1/295* (2006.01)
*G02B 6/12* (2006.01)

(52) U.S. Cl. .................... 385/8; 385/10; 385/14

(58) Field of Classification Search ............. None
See application file for complete search history.

(56) References Cited

U.S. PATENT DOCUMENTS

| 4,902,088 A | * | 2/1990 | Jain et al. ............... 385/8 |
| 5,276,745 A | * | 1/1994 | Revelli, Jr. ............. 385/14 |
| 5,761,350 A | * | 6/1998 | Koh ....................... 385/14 |
| 6,381,490 B1 | | 4/2002 | Ostrovsky |
| 6,385,355 B1 | | 5/2002 | Nashimoto et al. |
| 2003/0040134 A1 | | 2/2003 | Deliwala |

FOREIGN PATENT DOCUMENTS

FR 2 764 398 A1 12/1998
WO PCT/US2005/006829 6/2005

* cited by examiner

*Primary Examiner*—Sung Pak
*Assistant Examiner*—Omar Rojas
(74) *Attorney, Agent, or Firm*—Blakely Sokoloff Taylor & Zafman, LLP

(57) ABSTRACT

According to embodiments of the present invention, an ultra high speed miniature image acquisition system based on a scanning light beam for use with clinical endoscopic imaging applications, for example, is disclosed. In one embodiment, the image acquisition system may include a horizontal beam deflector disposed in an electro-optic polymer waveguide may disperse an incident light beam into a spectrum in a horizontal direction. A vertical beam deflector disposed in the waveguide and optically coupled to the horizontal beam deflector may deflect the horizontally dispersed spectrum in a vertical direction. An electrical charge may be applied to the electro-optic polymer.

26 Claims, 10 Drawing Sheets

POLYMER BASED ELECTRO-OPTIC SCANNER FOR IMAGE ACQUISITION AND DISPLAY

CROSS REFERENCE TO RELATED APPLICATIONS

This application claims the benefit of U.S. Provisional Application No. 60/548,930, filed Mar. 1, 2004.

BACKGROUND

1. Field

Embodiments of the present invention relate to image acquisition and, in particular, to flexible scopes for image acquisition.

2. Discussion of Related Art

Flexible scopes are commonly used in medical applications to look inside the human body to check the status of such organs as lungs, intestines, and colon, for example. Presently available flexible scope designs use either a bundle of optical fibers, typically in a tube, and/or one or more cameras having an array of detectors to capture an image.

All commercially available scopes suffer from a fundamental tradeoff between high image quality and small size, however. For example, the diameter of currently available flexible scopes cannot be reduced to smaller than the image size, and is limited by the individual pixel size of a camera or by the diameter of optical fibers used to acquire the image. Currently, the smallest pixel element is determined by the size of the end of an optical fiber, which has a minimum core diameter of about four micrometers (4 µm). To propagate light through an optical fiber, a surrounding cladding layer is required, increasing the minimum pixel size to more than 5 µm in diameter. If a standard video graphics adapter (SVGA) image is desired, (e.g., with a resolution of 640× 480 pixels), then a minimum diameter required for just the imaging optical fiber is more than three millimeters (3 mm). Larger diameters adversely affect the fineness of detail that can be distinguished in an image or resolution. Larger diameters also adversely affect the area that is visible through the scope or field of view (FOV). Therefore, to achieve scopes with less than 3 mm overall diameter using current technologies, resolution and/or FOV must be sacrificed by having fewer pixel elements.

Currently available scopes also suffer from poor control mechanisms. Some optical systems use an optical fiber and charge coupled device (CCD) camera at a tip of a flexible scope to illuminate a region of interest and acquire an image. The optical fiber and camera are manually controlled by a practitioner positioning the tip of the flexible scope. Other optical systems use a resonant fiber that is actuated into resonance with one or more nodes to produce a desired illumination spot. Although these systems actuate the fiber, such systems cannot precisely control the position of the fiber tip without adding material to the fiber scan system and increasing the diameter and/or tip length.

Other optical systems deflect or move mirrors to position the light beam rather than move the waveguide. However, the mirrors must be larger than the light beam diameter to avoid clipping the beam or adding diffraction. Thus, the mirrors must be larger than the waveguide, thereby increasing the overall size of the instrument.

Some microscopes actuate a cantilever waveguide for near-field imaging. However, near-field systems have a very limited field of view (FOV) (e.g., typically less than 500 nanometers), and a light-emitting tip must be positioned within nanometers of the target. Near-field systems are based on emitting light through a microscopic aperture with dimensions smaller than the wavelength of visible light. The emitted light reflects off the closely positioned target and is detected before the light has time to diffract and dissipate. A near-field system may be useful for imaging individual cells or molecules, but is not suitable for most medical procedures and other dynamic applications, which require a field of view (FOV) of at least a micron and can not be dependant on precisely positioning a tip within nanometers of a target. Using larger wavelengths to provide a suitable field of view (FOV) with a near-field system would still require a substantially larger imaging system, which could not be integrated into a multi-function instrument.

The concept of a micro-machined scanning optical microscope has also been explored in the form of confocal scanning microscope designs that employ a resonant XY bimorph stage, a resonant cantilever probe and lens, or at least one resonant micro-mirror. The confocal design for image acquisition has the advantage of spatially filtering the backscattered light while using the same optical fiber for illumination and signal collection. However, the extremely low efficiency of light collection (into the core diameter, typically few microns) of this design remains a disadvantage. Furthermore, confocal systems are limited to single wavelength operation, which does not enable color imaging or display.

SUMMARY OF THE INVENTION

Embodiments of the present invention are directed to a two-dimensional image scanner. In one embodiment, the scanner includes a horizontal beam deflector coupled to a vertical beam deflector. The horizontal beam deflector and the vertical beam deflector are disposed in a waveguide made of electro-optic polymer. In one embodiment, the horizontal beam deflector includes a cascaded grating prism (grism) array. In another embodiment, the horizontal beam deflector includes a cascaded right angle prism array. In another embodiment, horizontal beam deflector includes a cascaded convex or concave prism array. An output of the first horizontal beam deflector in the array is optically coupled to the input of the next horizontal beam deflector in the array via the waveguide. The output of the last horizontal beam deflector in the array is optically coupled to the input of the vertical beam deflector via the waveguide. In one embodiment, the vertical beam deflector includes a Bragg grating coupler disposed in the waveguide. A controller may causes an input voltage supply to drive the horizontal and vertical beam deflectors in a pattern relative to the target so as to display an image on the target and acquire an image of the target.

In one embodiment, the horizontal beam deflector array disperses an incident light beam into a spectrum (colors, wavelengths) in a horizontal direction and the Bragg grating coupler deflects the light from the horizontally dispersed spectrum having the Bragg grating wavelength in a vertical direction. An electrical charge is applied to the waveguide to change the Bragg grating wavelength so that the wavelength that exits the waveguide changes.

In one embodiment, a light source may be optically coupled to the horizontal beam deflector array. The light source may provide the light beam to the horizontal beam deflector array and may comprise several color elements each of which may produce a different color light. In another embodiment, a detector array may be optically coupled to the Bragg grating coupler. The detector array may detect the light having the Bragg wavelength.

Electro-optical scanning according to embodiments of the present invention offers a sensitive and accurate method to capture high-resolution images of physical and biological tissues. The minute physical size of such an electro-optical imaging system also offers a much needed advantage over conventional imaging systems. Yet, to date, there has been no capitalization on this technology, to enhance the performance of endoscopes, for example.

Embodiments of the present invention are directed to an ultra high speed miniature image acquisition system based on a scanning light beam that will be implemented for clinical endoscopic imaging applications. The system, which includes the integrated polymer waveguides, Bragg gratings, and the electro-optic beam steering device for horizontal and vertical beam steering, has high resolution and field-of-view (FOV). The beam deflection is based on the fact that the propagation direction of the light beam is changed when it is incident to an electro-optic medium where the index is changed by the applied electric field. Embodiments of the invention greatly impact the state-of-the-art of clinical endoscopic imaging and low cost optical scanners that are only a few millimeters long and that fit inside endoscopic tubes with diameters of less than 1 mm. This size will enable users to examine areas anatomically inaccessible by currently designed endoscopes, reduce collateral damage to tissue, and enable integration of imaging with other functional devices, such as therapy and diagnostic devices, for example.

Another feature of embodiments of the present invention is that scanning is accomplished via changing the Bragg wavelength using electrical means rather than using a moving waveguide. This means that the illuminating light spot is not dependent on the dynamics of the waveguide. As a result it is easy to predict and control the exact location of the illuminated spot, making image quality not an issue. Also, the maximum scanning frequency is increased, sensitivity to external vibration and thermal variations is reduces, and field of view (FOV) is improved.

Another feature of embodiments of the present invention is its small size and flexibility. For example, in one embodiment the scope is has at least two dimensions of less than approximately on millimeter (1 mm) in diameter and has a tip deflection capability of 90° or greater in a single plane in either forward/backward or side to side direction. A significantly smaller and more flexible endoscope will advance the burgeoning field of minimally invasive medical techniques. A smaller scope also will allow doctors to see within body cavities that were previously inaccessible using conventional equipment. Also, a smaller scope provides more space for biopsy forceps, grasping forceps, surgical scissors, etc, and could make unsedated endoscopy procedures more probable. Without having to use sedation and analgesia during endoscopy reduces the risk of complications for many individuals in whom intravenous sedation is undesirable. The patients also avoid the prolonged recovery intervals due to the medications.

Another feature of embodiments of the present invention is that it resolves some of the problems with mechanical systems, such as mechanical fatigue, nonlinear dynamic effects at large fields of view (FOV), mechanical instability (no feedback, prompt to ambient vibration), signal drift, and fixed and low spatial resolution. For example, high scanning speeds (gigahertz range) increase spatial resolution in that it provides more lines per scan. SVGA image or greater resolution is easily obtained without increasing the overall design size. In embodiments, the resolution may be much greater than the currently available highest resolution endoscopes that have approximately 850,000-pixels.

Another feature of embodiments of the present invention is the ability to create a large field of view (FOV), such as greater than approximately ninety degrees (>90°) and a variable FOV. This is made possible by the fact that the input voltage to the beam deflectors (or electrical charge applied to the electro-optic polymer) will electronically control the scanning angle.

Another feature of embodiments of the present invention is the ability to transmit multiple wavelengths and variable zoom without loss of resolution (large depth of field). This is made possible by the broadband frequency response and voltage control of the electro-optic actuators, such as, for example, actuators made of a material that can be manipulated mechanically by an applied electromagnetic field, for light beam deflection. The focus adjustment procedure is significantly simplified due to the voltage control beam deflector, thus ensuring speedy observation. Optical magnification is also simplified due to the fact that the zoom-in and zoom-out functions are now controlled by the displacement and the line resolution of the voltage controlled beam deflectors.

The use of MEMS fabrication processes also offers advantages in that it allows for the integration of light sources, scanners, sensors, detectors, and electronics on a single chip configuration. This reduces the overall size and the power consumption of the system, while improving the signal to noise ratio, bandwidth and image quality. Batch processing also enables the production of a high quality product at low cost. This opens the door for design of disposable surgical imaging devices.

Future portable endoscope systems may be made possible by the proposed integrated image system. With this system, an edoscopic procedure will be performed without sedation of the patient and will be operated from a laptop or a portable monitoring system. Physicians may also be able to examine patients in emergency field settings.

BRIEF DESCRIPTION OF THE DRAWINGS

In the drawings, like reference numbers generally indicate identical, functionally similar, and/or structurally equivalent elements. The drawing in which an element first appears is indicated by the leftmost digit(s) in the reference number, in which.

DETAILED DESCRIPTION OF THE
ILLUSTRATED EMBODIMENTS

Figure 1:
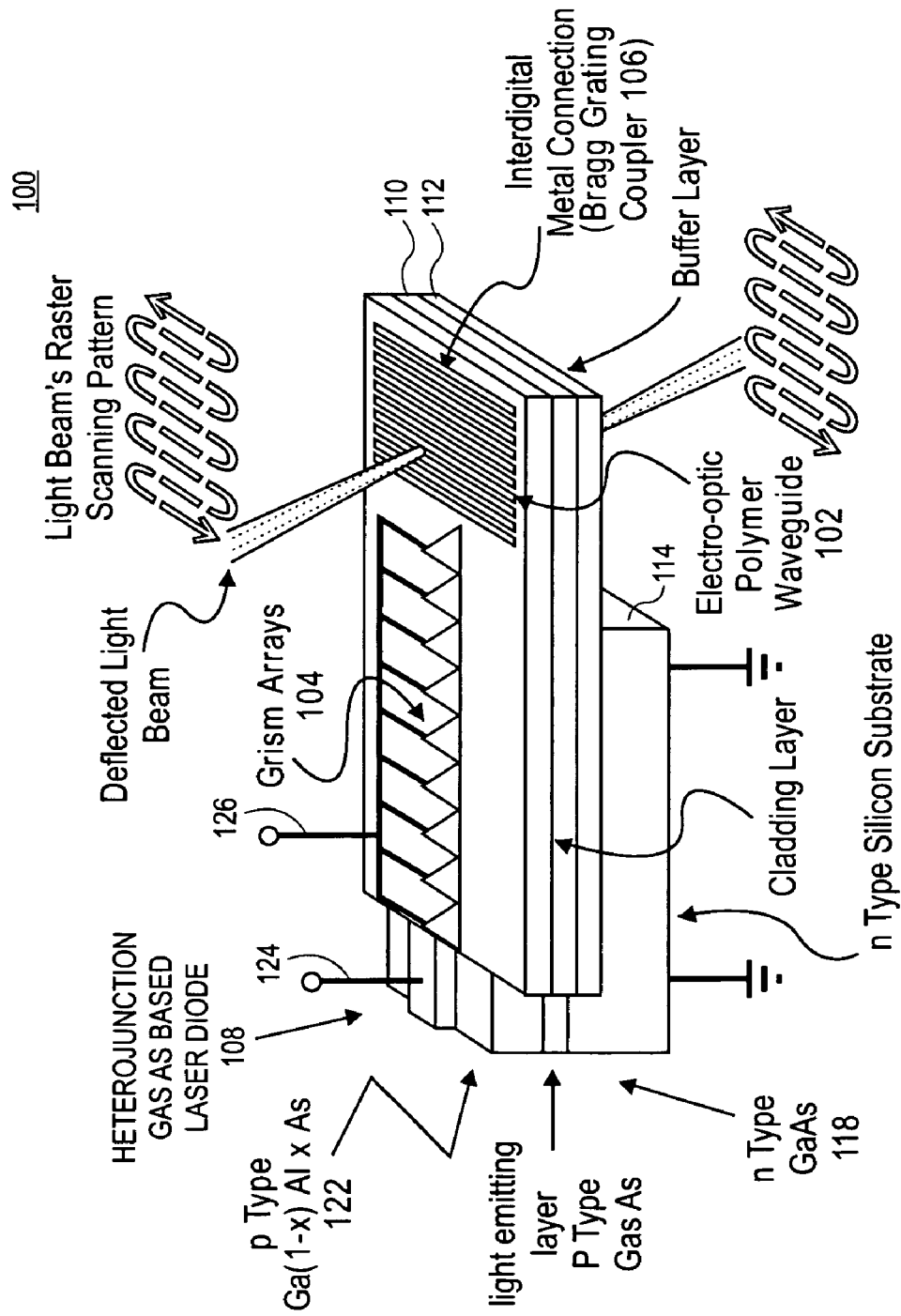
FIG. 1 is a perspective diagram of an electro optic scanner according to an embodiment of the present invention.

FIG. 1 is a cross-section diagram of a two-dimensional electro-optic scanner 100 according to an embodiment of the present invention. In the illustrated embodiment, the scanner 100 includes an electro-optic waveguide 102 having a cascaded horizontal beam deflector array 104 and a Bragg grating coupler 106 disposed thereon. The example horizontal beam deflector array 104 includes nine individual horizontal beam deflectors, each of which includes a prism and a transmission grating disposed on the hypotenuse of the prism.

In the illustrated embodiment, the electro-optic scanner 100 is a multi-layer structure. The first a layer 102 is a layer of electro-optic polymer, a second layer 110 is a layer of optical material with slightly lower index of refraction n than the index of refraction of the layer 102 of electro-optic polymer, a third a layer 112 is a layer of optical material that serves as buffer layer to prevent light coupling from the electro-optic (core) layer 102 into a fourth layer 114 of silicon substrate. In one embodiment, the silicon substrate layer 114 may be a highly doped N-type silicon substrate that serves as ground for the scanner 100. The layer 102 may include a metal thin film layer patterned in a series of identical horizontal beam deflectors to form the beam deflector array 104. The two cladding layers 110 and 112 are made of polymer with refractive index slightly lower than the waveguide layer 102. The waveguide core layer 102 forms the propagating waveguide and has the special attribute of possessing the electro-optic effect when a large electric field and heat are applied to the polymer material in the layer 102 to make it electro-optically active. The top electrode 126 is patterned like a bottom electrode 124 with the base of the electrodes interconnected for electric continuity.

Figure 7:
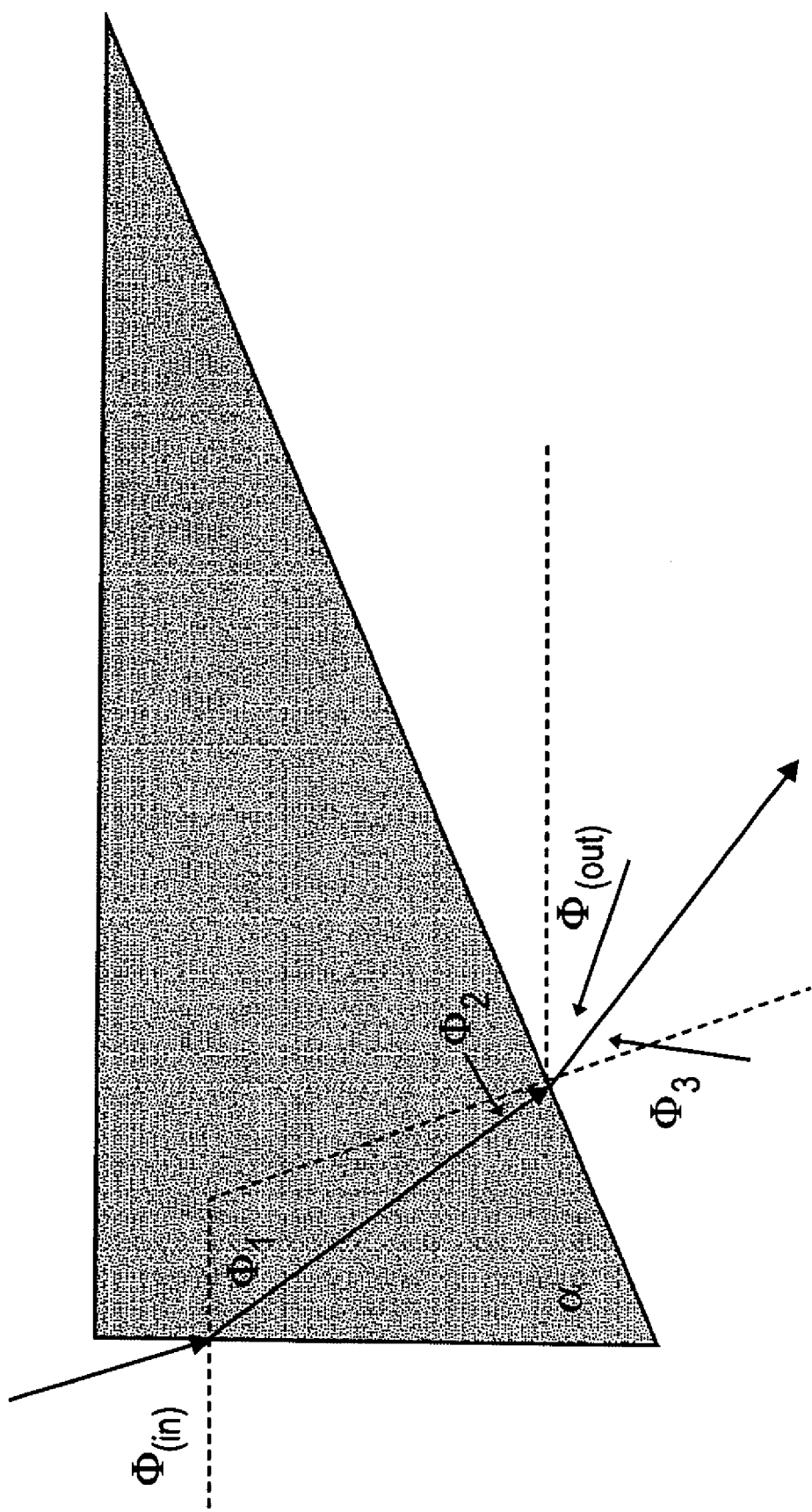
FIGS. 7–9 illustrate ways of implementing horizontal beam deflectors according to alternative embodiments of the present invention.
Figure 8:
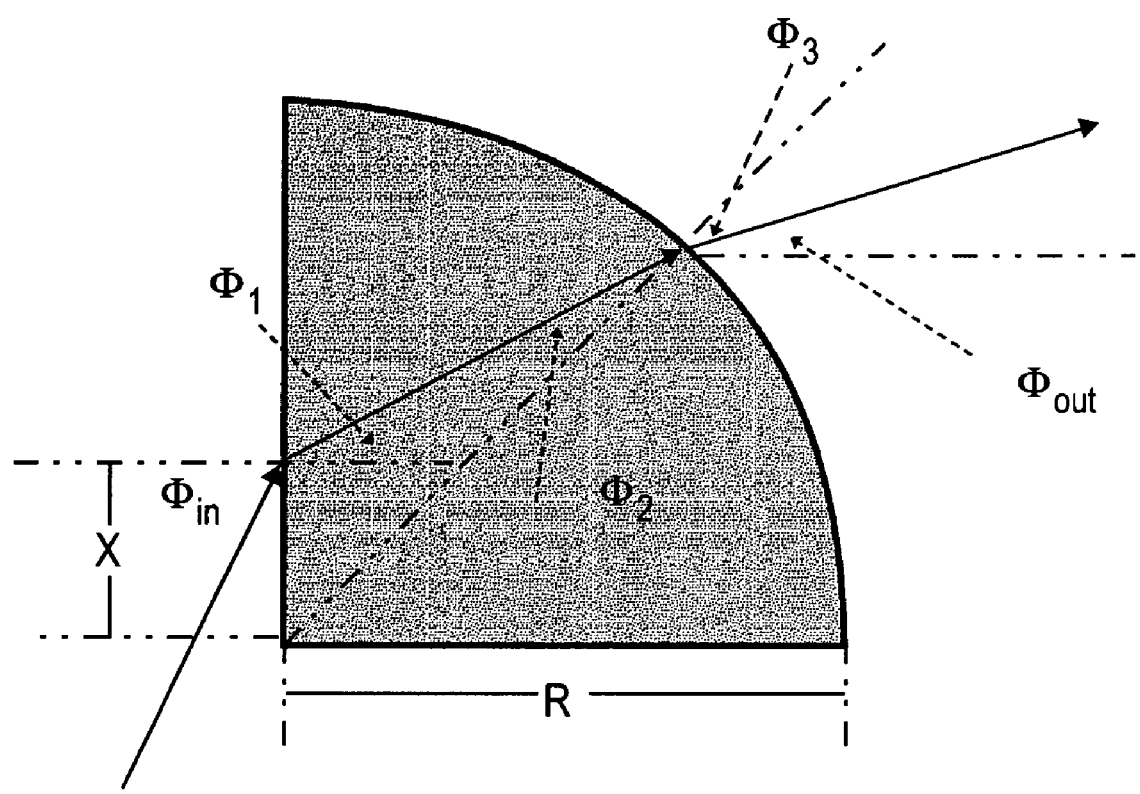
Figure 9:
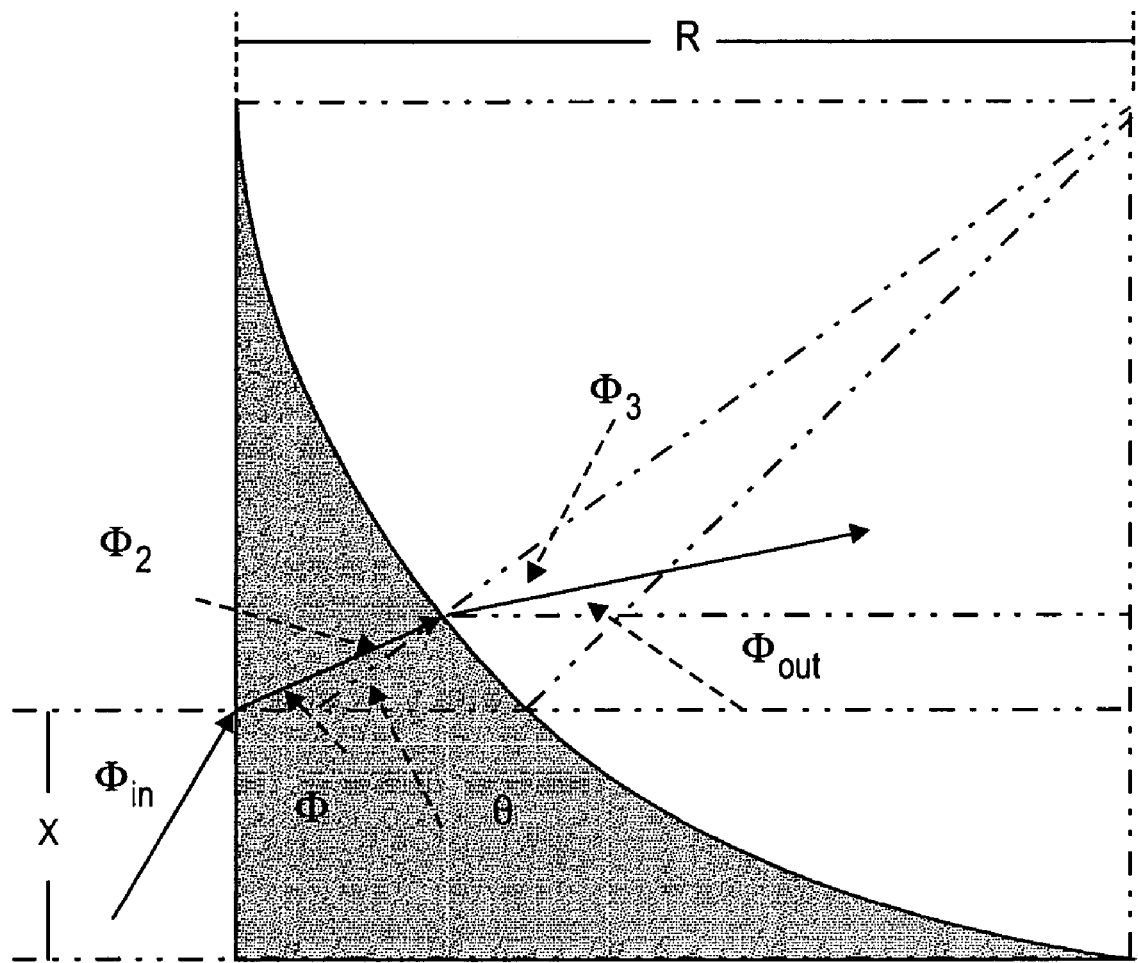

FIGS. 7–9 illustrate alternative horizontal beam deflector 104 embodiments. FIG. 7 illustrates a horizontal beam deflector 104 implemented using a right angle prism pattern. FIG. 8 illustrates a horizontal beam deflector 104 implemented using a convex prism pattern. FIG. 9 illustrates a horizontal beam deflector 104 implemented using a concave prism pattern.

Beam steering devices without moving parts, such as the electro-optic scanner 100, are highly desirable in an image acquisition and image display system. In the electro-optic scanner 100, the propagation direction of an incident light beam is changed when the index of refraction of the electro-optic medium 102 is altered by the application of an electric field. In one embodiment, an electric field may be applied via a voltage applied on the top electrode 126 and bottom metal electrode 124. The horizontal motion of the scanner 100 is controlled by the horizontal beam deflector array 104 while the beam is deflected vertically by the electro-optic Bragg grating coupler 106.

For the horizontal beam deflector array 104, the applied electric field from the grism's, convex prism's, or concave prism's shaped electrodes induces a variation of index of refraction in the core layer 102 that is made of electro-optic polymer. Light propagating through this grism array 104 deviates from its original path at the interfaces between adjacent regions because of the different indices of refraction. The output from the grism array 104 may then be steered by applying an input voltage to the electrodes at a terminal 126.

Light incident on a grism 104 is dispersed by the prism and further diffracted by the gratings. The mathematical relationship between the wavelength and the angles of incident φ and diffraction in a given spectra order m, is given in as $$m\lambda = d(n' \sin \phi + n \sin \beta)$$

where n'=n+Δn and n are refractive indices of the electro-optic material inside and outside the grism array 104. The refractive index change Δn(x, y, z) due to an applied voltage, V, in the small electrode gap region is equal to $$\Delta n = n^3 \gamma_{33} kV$$

where n is the electro-optic refractive index, $\gamma_{33}$ is the electro-optic coefficient for the core structure, k is the proportionality constant which depends on the overlap factor of the voltage-induced applied electric field and the guided optical mode profile. M. D. Himel, X. Shi, X. Q. Hu, M. G. Moharam and K. H. Guenther, "Eletrooptic beam deflection using the leaky mode of a planar waveguide," IEEE Photonics Technol. Lett., Vol. 3, p. 921–923, 1991 and/or T. Tamir and S. T. Peng, "Analysis and Design of Grating Couplers," Applied Physics, Vol. 14, p. 235–254, 1977, are both incorporated herein by reference.

With the active grism array 104 where the indexes of refraction inside of grism array 104 are actively controlled by input voltage, the deflected angle is therefore, $$\beta(\lambda) = arc \sin (m\lambda d - n' \sin \phi)/n)$$

For the current grisms type deflector, the maximum diffracting angle is around 1 degree with 1% optical index change when the beam travels from electro-optic polymer to air. The diffraction angle is less (0.8°) when light is passing from electro-optic polymer to non-activated EO substrate (assuming index of refraction ~1.65). In embodiments of the invention, a large deflection occurs when the light beam passes through the grism array 104.

The concept of the electro-optic grating is similar to the grisms technique where the beam is deflected by the electro-optically induced index change. The difference is that its device consists of a channel waveguide and a periodic electrode. An applied modulated signal on the electrode creates a periodic index-modulated grating in the propagation direction of the guided optical wave. The propagating modes interact with the index-modulated grating and are coupled with the phase matching radiating mode of the substrate or of air. Thus the exit angle becomes a function of optical index change.

The same beam deflection can be accomplished by using a prism. Light incident on a prism is dispersed by the prism and a mathematical relationship between the incident φ and output angle β is given as $$\beta = \sin^{-1}\left(\frac{n'}{n_{output}}\sin\left(\alpha - \sin^{-1}\left(\frac{n_{input}}{n'}\sin\phi\right)\right)\right)$$

where $n_{input}$=refractive index of input medium, $n_{output}$=refractive index of output medium, $n'=n+\Delta n$ and $n$ are refractive indices of the electro-optic material inside and outside the prism array 104. The refractive index change $\Delta n(x,y,z)$ due to an applied voltage, V, in the small electrode gap region is equal to $$\Delta n = n^3 \gamma_{33} kV$$

where n is the electro-optic refractive index, $\gamma_{33}$ is the electro-optic coefficient for the core structure, k is the proportionality constant which depends on the overlap factor of the voltage-induced applied electric field and the guided optical mode profile.

For the current right angle prism type deflector, the diffracting angle is around 6.4 degree with 0.1% optical index change when the beam travels from electro-optic polymer (n=1.65) to air. A large deflection occurs when the light beam passes through the convex prism array illustrated in FIG. 8.

For the same horizontal beam deflector done by the right angle prism illustrated in FIG. 7, light incident on a prism is dispersed by the prism and a mathematical relationship between the incident $\phi_{in}$ and output angle β is given as $$\phi_1 = \sin^{-1}\left(\frac{n_{input}\sin\beta}{n}\right)$$

$$\phi_2 = \sin^{-1}\left(\frac{X\sin(\phi_1 + 90°)}{R}\right)$$

$$\phi_3 = \sin^{-1}\left(\frac{n\sin\phi_2}{n_{output}}\right)$$

$$\beta = \phi_1 + \phi_2 - \phi_3$$

where X is the location on the incident side of the prism from the base, R is the radius of the convex curvature, $n_{input}$=refractive index of input medium, $n_{output}$=refractive index of output medium, $n'=n+\Delta n$ and $n$ are refractive indices of the electro-optic material inside and outside the prism array 104. The refractive index change $\Delta n(x,y,z)$ due to an applied voltage, V, in the small electrode gap region is equal to $$\Delta n = n^3 \gamma_{33} kV$$

where n is the electro-optic refractive index, $\gamma_{33}$ is the electro-optic coefficient for the core structure, k is the proportionality constant which depends on the overlap factor of the voltage-induced applied electric field and the guided optical mode profile.

For the current convex prism type deflector, the diffracting angle is around 6.5 degree with 0.1% optical index change when the beam travels from electro-optic polymer (n=1.65) to air. A large deflection occurs when the light beam passes through the convex prism array.

For the same horizontal beam deflector done by a concave prisms, light incident on a prism is dispersed by the prism and a mathematical relationship between the incident $\phi_{in}$ and output angle β is given as $$\phi_1 = \sin^{-1}\left(\frac{n_{input}\sin\beta}{n}\right)$$

$$\phi_2 = \sin^{-1}\left(\left(1 - \frac{X}{R}\right)\cos\phi_1 - \sin\phi_1\right)$$

$$\phi_3 = \sin^{-1}\left(\frac{n\sin\phi_2}{n_{output}}\right)$$

$$\beta = \phi_1 + \phi_2 - \phi_3$$

where X is the location on the incident side of the prism from the base, R is the radius of the concave curvature, $n_{input}$=refractive index of input medium, $n_{output}$=refractive index of output medium, $n'=n+\Delta n$ and $n$ are refractive indices of the electro-optic material inside and outside the prism array 104. The refractive index change $\Delta n(x,y,z)$ due to an applied voltage, V, in the small electrode gap region is equal to $$\Delta n = n^3 \gamma_{33} kV \quad (5)$$

where n is the electro-optic refractive index, $\gamma_{33}$ is the electro-optic coefficient for the core structure, k is the proportionality constant which depends on the overlap factor of the voltage-induced applied electric field and the guided optical mode profile.

For the current concave prism type deflector, the diffracting angle is around 5.1 degree with 0.1% optical index change when the beam travels from electro-optic polymer (n=1.65) to air. A large deflection occurs when the light beam passes through the concave prism array illustrated in FIG. 9.

The vertical direction deflector is based on the principle of electro-optically induced grating coupling of guided optical modes to substrate modes. As schematically shown in FIG. 1, the device consists of the waveguide channel 102 and a periodic electrode or Bragg grating coupler 104. An applied modulated signal on the grating coupler 104 creates a periodic index-modulated Bragg grating in the propagation direction of the guided optical wave. The propagating modes interact with the index-modulated Bragg grating and are coupled phase matching radiating mode of the substrate. Thus the exit angle out of the waveguide 102 becomes a function of optical index change.

For the vertical beam deflection, the Bragg grating coupler 104 perturbs the waveguide modes in the region underneath the grating, thus causing each one of them to have a set of a spatial harmonics. The grating scatters the incoming energy into space-harmonic fields that vary as $\exp[i(k_{xn}x - \omega t)]$ where $k_{xn}$ is related to grating period d by:

$$kxn = \beta_v + j\alpha = \beta_o + 2\pi v/d + j\alpha, \text{ where } v \text{ is } 0, \pm 1, \pm 2, \ldots$$

Unless permittivity of the grating is much larger than the permittivity of the film, the fundamental term $\beta_o$ is closely equal to $\beta_{sw} = (2\pi n/\lambda) > k_o = 2\pi/\lambda$ of the propagating surface wave since the α factor is usually small. The α factor is due to the leakage of the energy into the diffracted orders scattered by the grating. Because of this the leakage, each scattered field is in the form of a leaky-wave beam. These waves radiate into the air region at an angles $$\Phi_v = \sin^{-1}(\beta_v/k_o), \text{ where } v \text{ is } 0, \pm 1, \pm 2, \ldots$$

M. D. Himel, X. Shi, X. Q. Hu, M. G. Moharam and K. H. Guenther, "Eletrooptic beam deflection using the leaky mode of a planar waveguide," IEEE Photonics Technol. Lett., Vol. 3, p. 921–923, 1991 and/or T. Tanir and S. T. Peng, "Analysis and Design of Grating Couplers," Applied Physics, Vol. 14, p. 235–254, 1977, are both incorporated herein by reference.

Since we are only interested in single outgoing beam into the upper air region, the grating period, d, must be carefully selected such that $|\beta_v|>k_o$ for all $v \neq -1$. In the substrate region, there is a corresponding beam that exits into lower air region, but the following condition $|\beta_{-1}>k_o n_s|$ (where $n_s$ is index of refraction of the substrate) must be also satisfied to reduce unnecessary loss due unwanted high-order surface wave modes traveling in the substrate region.

With the active Bragg grating coupler 104, the vertical diffracting angle will vary with the change in the index by the input voltage. The existing angle and the range are carefully controlled by the grating period and the index of refraction of the electro-optic material.

In one embodiment, the material for the electro-optic polymer may be polystyrene-based Diels-Alder cross-linkable NLO polymers with a TCF-type chromophore thin film. This material provides high electro-optical coefficient, is thermally and photo-chemically stable, and has low loss stemming from absorption, impurity scattering, and surface scattering. The cladding 110 may be made of a material such as Noland 63 and Noland 61. The choice for the electrodes 124 and 126 is gold deposited thin film.

In embodiments of the invention, a commonly used laser holography technique for sub-micron level lithography may be used for the grating construction. The Bragg grating coupler 106 structure may be formed by first exposing a 488 nm wavelength (Argon laser) or 325 nm (Helium Cadmium Laser) UV interference pattern on a photosensitive polymer such as positively toned Ultra123 and negatively toned Su-8, (MicroChem Corp., MA) and placed on top of a silicon substrate to form the master. The film may be subsequently developed and have a periodicity of fringes on the film. Although there are many techniques of exposing the interference patterns to form the Bragg grating coupler 106, one embodiment may use a classical Lloyd's mirror interferometer. The interference fringes of constant spatial frequency are formed when a monochromatic, plane wave front is spatially divided in half by plane mirror and the two halves are superimposed later when the two are converged on the photosensitive polymer. The spatial frequency ν (fringes/mm) only depends on wavelength, λ, and the angle, φ, at which the two wave fronts interfere, which is expressed as $v=2 \sin \phi/\lambda$.

In the illustrated embodiment, a light source 108 is integrated into the scanner 100. The light source 108 also is a typical GasAs based heterostructure laser diode. In the fabrication of this device 108, the anomalously fast diffusion of Zn in GaAs is utilized to form a diffused p-n junction lying 1 to 2 □m below the $Ga_{(1-x)}$ $Al_x As$ 122 and n type GaAs 118 heterojunction. Optical confinement occurs only on one side of the light emitting junction, at the interface between the p type GasAs 120 and $Ga_{(1-x)}$ $Al_x As$ 122. The top metal electrode 126 and bottom metal electrode 124 layer provide the contact points between the diode 108 and the power supply. In one embodiment, the light source 108 may also include a tunable color filter to provide precise color spectrum of light (i.e. RGB), the tunable color filter comprising one of an optical resonant cavity, a grating, and a prism.

Methods of coupling a light beam into a thin-film waveguide are well established. In many cases, it is necessary to couple light into a waveguide that is buried within the device, with only the surface or the end exposed. In one embodiment, the input light source 108 will either be a pigtail laser light source or a semiconductor laser. Therefore, it is important to use techniques appropriate for each coupling condition.

The end-butting coupling (or mechanical coupler) method is practical in case of coupling the waveguide 102 to the light source 108. The direct end-butt method is capable of efficiently coupling an un-collimated divergent laser beam (10 to 20°) emitted from a semiconductor laser, which is difficult to achieved using either prism, grating, or tapered film couplers. High efficient coupling is achieved by making the thickness of the waveguide 102 approximately equal to that of the light emitting layer 202 of the laser 108 and aligned as shown in FIG. 2a, and also by the fact that the field distribution of the fundamental lasing mode is matched to the $TE_0$ waveguide mode. The efficiency is further improved if indices of the light emitting layer 202 and waveguide 102 are close and the ratio of the thickness of waveguide 106 to the light emitting layer 202 is small. To eliminate any oscillatory shape of output due to the Fabry-Perot etalon formed by the plane parallel faces of the laser 108 and waveguide 102 (when separation between them are less than a wavelength), epoxy of the matching index between the laser and waveguide must be used. This method is useful if an unpackaged laser diode is used.

Figure 2B:
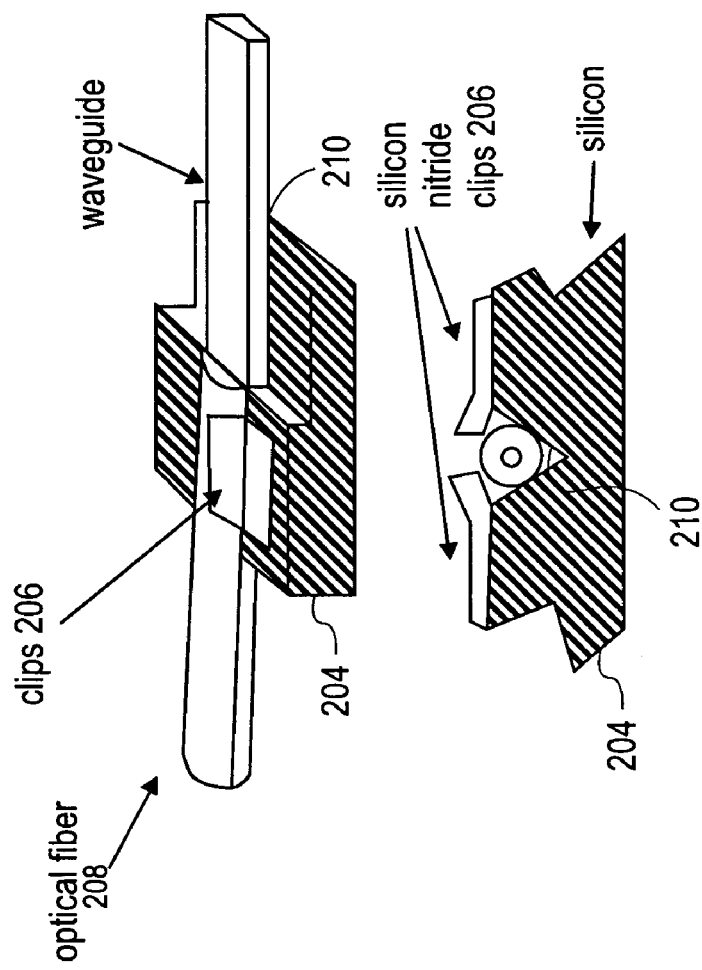
FIG. 2(b) is a perspective diagram of V-groove optical fiber coupling of a light beam into a waveguide according to an embodiment of the present invention.
Figure 2A:
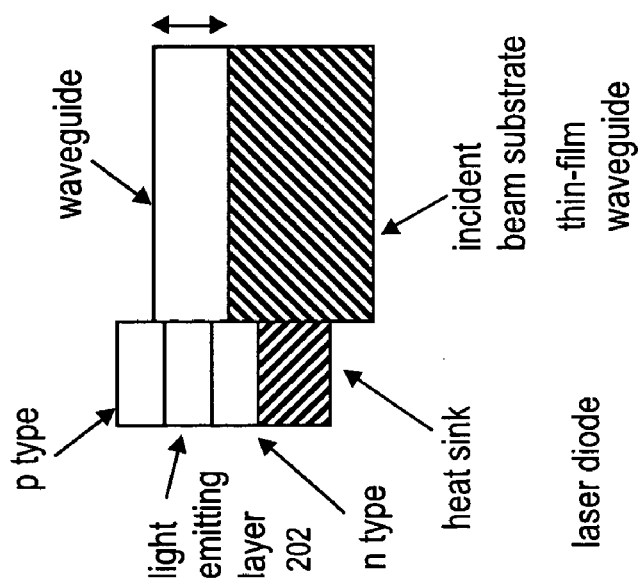
FIG. 2(a) is a perspective diagram of end-butt coupling of a light beam into a waveguide according to an embodiment of the present invention.

If a pigtail laser is used as the light source 108 and is coupled to the semiconductor waveguide 102 a silicon V groove coupler 204 with silicon nitride clips 206 as shown in FIG. 2b may be used. The advantage of using clips 206 instead of glue or metal welding for connection is its simplification of the coupling manufacturing process. Without gluing or welding, the optical fiber 208 easily sits in the v-shape groove 210 in silicon that is made by wet etching and held by the set of silicon nitride clips 206. These clips 206 are typically manufactured by vapor deposition and wet etching.

Integration of a photodetector 301 into the same chip with the rest of the electronics affords several advantages. The stability of the receiver is improved, because the large parasitic capacitance and inductance between the photodetector and the input to the transimpedance preamplifier (not shown) are reduced drastically. In addition, the bandwidth is increased and the noise, size and mechanical complexity reduced. Production costs may also be lower, because the number of components decreases if the photodetector is integrated into the same process without any process modifications.

In one embodiment, the photodetector 301 may be constructed from a silicon substrate. The material may also be the substrate used in the waveguide and beam deflectors. The silicon photodiode is known for light wave detection in the wavelength ranges of 0.4 to 1 μm due to its high responsibility around that wavelength spectrum. It has the virtues of high quantum efficiency, good linearity of response, large bandwidth, simple bias option and relatively easy to fabricate. Since pairs of red, green and blue photodetectors are required for capturing color images, these silicon based photodiodes offer the sufficient bandwidth in the visible spectrum (photodetector bandwidths must exceed 12.5 MHz for VGA and 19.8 MHz for SVGA video standard).

There are several methods for integrating the photodetector 301 on a silicon substrate. In one embodiment, the photodiode 301 is the depletion layer photodiode. The depletion-layer photodiode is essentially a reverse-biased semiconductor diode where reverse current is modulated by the electron-hole pairs produced in or near the depletion layer by the absorption of photons of light. The simplest depletion layer photodiode is a p-n junction diode. The diode is formed by boron diffusion (p-type silicon) to an n-type silicon substrate 303. A thick layer (several micrometers thick) of waveguide material made of either $SiO_2$ or silicon nitride is grown and used as a diffusion mask and later left as the waveguide. Metal electrodes 304 are then added to complete the structure.

To obtain a high current gain and maintain a high operating frequency, an avalanche photodetector (APD) structure may be implemented. In this device, a basic p-n structure is operated under a very high reverse bias. Setting precisely at the point of avalanche breakdown, carrier multiplication due to impact ionization results in significant gain in terms of increase in the carrier to photon ratio. The current multiplication for an avalanche diode can be as high as 4 orders in magnitude (based on commercially available photovoltaic photodiode and APD from UDT Sensor LTD).

Figure 3:
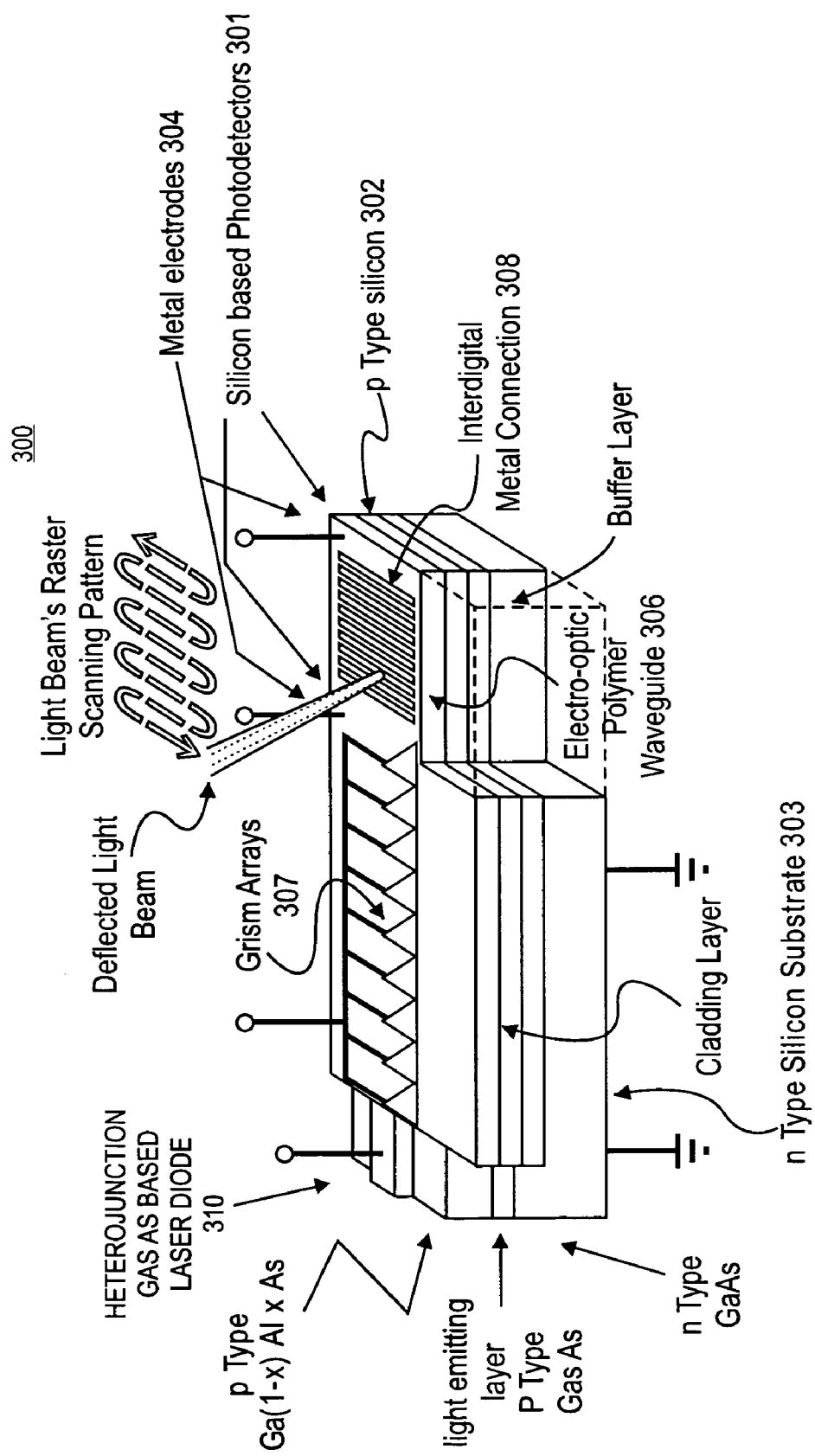
FIG. 3 is a perspective diagram of a monolithic integrated optical scanning apparatus according to an embodiment of the present invention.

A monolithic integrated optical scanning system 300 is shown in FIG. 3. The system 300 includes a waveguide 306 and an array of beam deflectors 307 and 308, where a light beam is emitted and the direction of propagation is displaced along two orthogonal directions by the array of grisms 307 and Bragg gratings 308. The image created from the back-scattered light is captured by an array of embedded p-n junction diodes 301 placed around the beam deflectors. If an unpackaged semiconductor laser 301 is used, the end-butting coupling (or mechanical coupler) method will be used. If a pigtail laser light source is used, a V groove with silicon nitride clips as shown in FIG. 2b will be used.

Embodiments of the present invention may be used to illuminate specific patterns for microlithography, micro-inspection, and micro-illumination. Embodiments of the present invention also may be used as optical switches, routers, etc. Embodiments of the present invention can further be embodied in a bar code reader, a range finder, or a device for combining simultaneous sensing and delivery functions. Some of the ideas are explained in details in the following sections.

Embodiments of the present invention may be used in mask-less photolithography applications. In one embodiment, the two-dimensional micro-scanner can also be used as a UV light writing device, which a pattern will be created by the light directly exposed on the photoresist. This is a very unique way of doing the photolithography because it does not require a chrome mask. There are many advantages of using this technique. First, the light steering device allows the user to create a pattern on photoresist quickly and accurately. Second, the light steering device allows multiple layers of pattern to be written on the photoresist without having to go through tedious alignment. Third, the design may be changed quickly without having to create a new mask. Fourth, intensity and optical beam size is controlled (this will allows user to expose different sizes of points, lines and areas.

Embodiments of the present invention may be used as an endoscope in minimally invasive medical procedures (MIMPs). The current tools used for MIMPs cannot readily be integrated with an optical imaging system without increasing the size of the resultant instrument. All currently available commercial optical imaging systems that include a maneuverable flexible shaft must maintain a certain size (diameter) in order to preserve image quality. Currently available flexible scopes cannot be made smaller than this limit unless image field-of-view or resolution is sacrificed. Thus, it would be highly desirable to create a smaller imaging system for the purpose of reducing the overall size of an instrument used for MIMPs and other applications. In embodiments of the present invention, the electro-optic scanner may be used as an imaging system that is small enough to be integrated with diagnostic and/or therapeutic functions to create an instrument that is sufficiently intuitive to use as to require little training or skill. The proposed image acquisition system integrates a light source, an actuation system, and light detectors, yet be smaller than currently available systems. Reduction of the imaging system reduces the overall size of endoscopes will provide more space for biopsy forceps, grasping forceps, surgical scissors, etc. Despite its small size, the integrated system is capable of providing a sufficient FOV, a good image size, and high resolution. Therefore this system will allow doctors to see within body cavities that were previously inaccessible or used to require incision.

Embodiments of the present invention may be used in un-sedated endoscopy procedures. Overall size reduction to a few mm could make unsedated endoscopy procedures more probable. Without having to use sedation and analgesia during endoscopy reduces the risk of complications for many individuals in whom intravenous sedation is undesirable. The patients also avoid the prolonged recovery intervals due to the medications.

Embodiments of the present invention may be used in portable endoscope systems. Future portable endoscope systems will be made possible by the proposed integrated image system. With this system, an edoscopic procedure will be performed without sedation and will be operated from a laptop or a portable monitoring system. Physicians will also be able to examine patients in emergency field settings.

Figure 4:
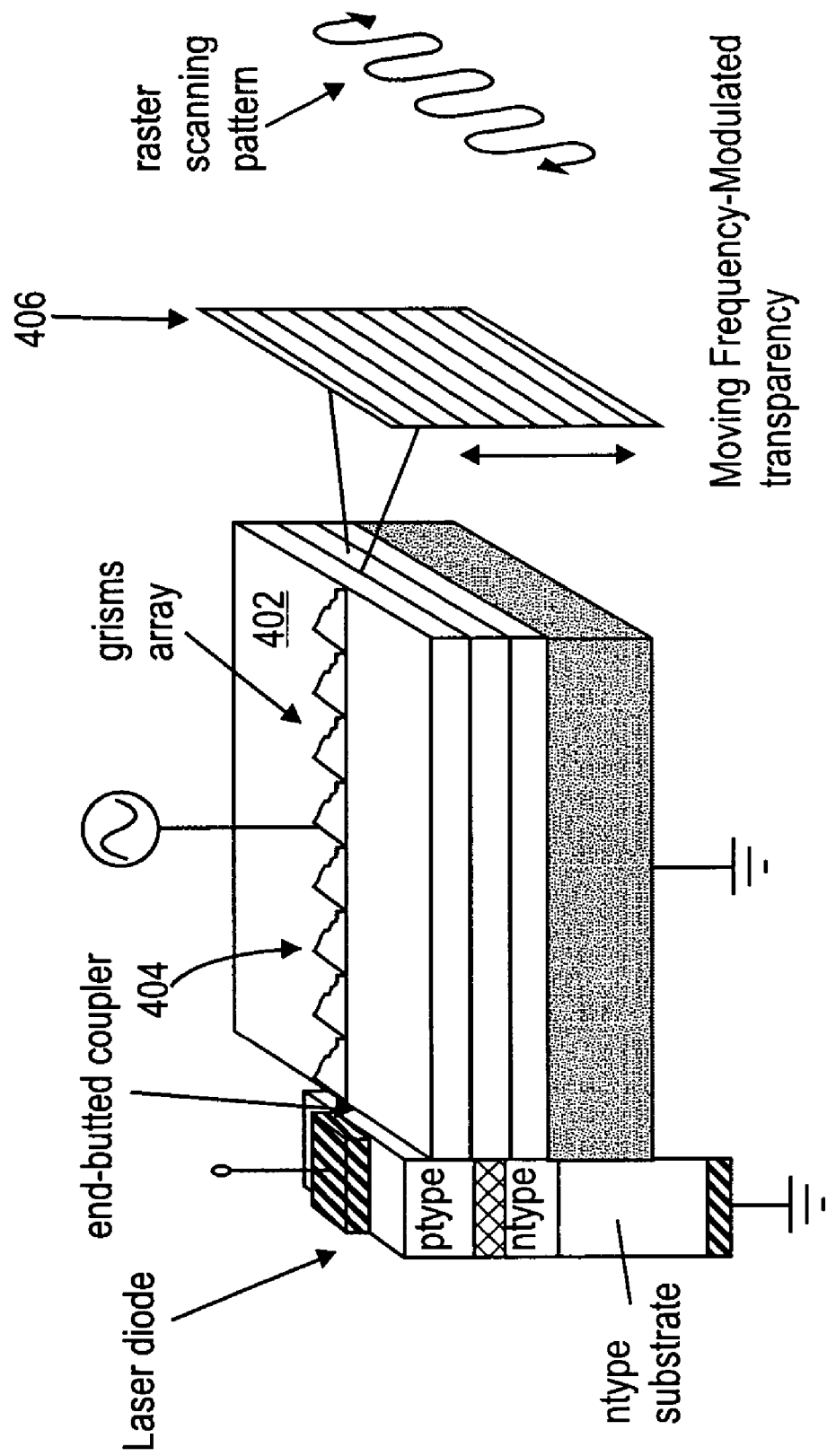
FIG. 4 is a perspective diagram of two-dimensional beam steering using frequency modulated transparency according to an embodiment of the present invention.

Embodiments of the present invention may be used in optical diagnostic and therapeutic devices. As an endoscope, the present invention can be used to integrate both imaging and non-imaging functionality, such as diagnosis, monitoring, and therapy of an internal region of interest, instead of requiring separate instruments for imaging and for rendering therapy or other functions to a site. For example, an integrated endoscope can provide ultra violet therapy and monitoring. Also, many optical diagnostic and therapeutic techniques rely on high quality illumination at elevated intensities, which is inherent in optical scanning and cannot be achieved with diffuse illumination. A scanned beam of intense optical energy is more effective at overcoming the signal-to-noise limitations of photon detectors used in conventional diagnostic imaging systems. When fluorescent dye molecules are used as tracers for specific cells or structures, the signal conversion rates from illumination to fluorescence are very low and often buried in noise. In many therapeutic applications, such as photodynamic therapy (PDT), the optical excitation of PDT labels on cancerous cells creates free radicals that kill nearby cells. Doses of intense optical illumination are applied to overcome the natural buffering mechanisms within the body, to attain effective concentrations of free radicals. Laser therapies that rely on optical heating, cutting, and cauterization of tissues require the highest optical intensities that can be delivered and cannot be used effectively with diffuse illumination. Directed, focused beams of light on tissue for precise exposure times are necessary for reducing surrounding tissue damage which is provided in a controlled optical scan system. Furthermore, high quality illumination can include a high degree of optical monochromaticity, coherence, polarization, high modulation frequency, high pulse repetition rates, and short pulse duration Embodiments of the present invention also may be used in other two dimensional beam steering applications using frequency-modulated transparency instead of electro-optically induced grating structure. Two-dimensional beam steering using frequency-modulated transparency remains an all optical process. In one embodiment, the basic design of the system may include a thin film electro-optic polymer waveguide 402 with built-in cascaded grisms 404 and a thin transparency 406 with complex amplitude transmittance as shown in FIG. 4. The horizontal motion may be controlled by the cascaded grisms 404 while the beam is deflected vertical by the frequency modulated grating structure 406.

Figure 5:
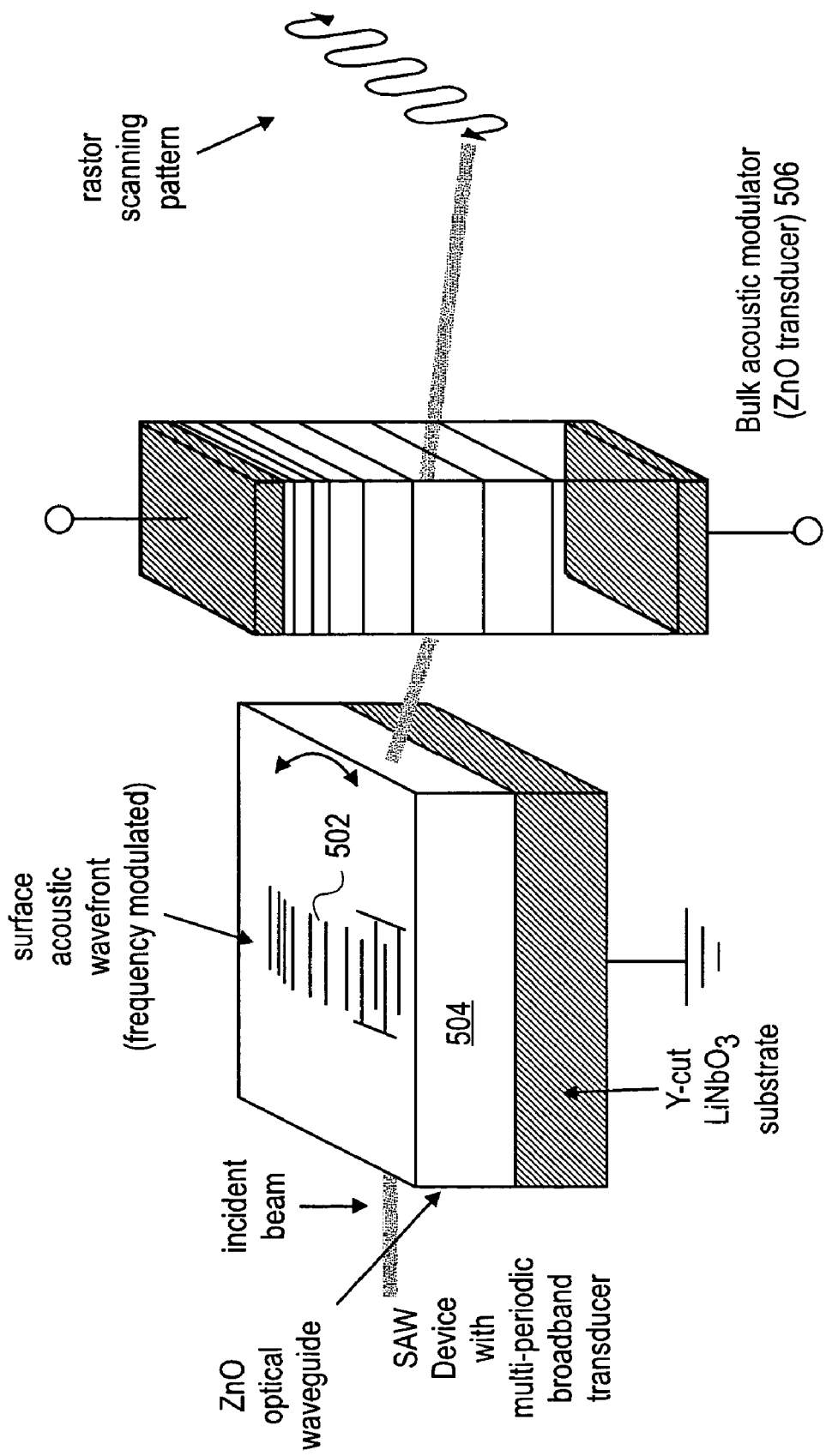
FIG. 5 is a perspective diagram of two-dimensional beam steering using a surface acoustic wave (SAW) device and a bulk acoustic modulator according to an embodiment of the present invention.

Embodiments of the present invention also may be used in other two dimensional beam steering applications using surface acoustic wave and bulk acoustic-optic modulators for beam deflection, for example. Two dimensional beam steering using surface acoustic wave and bulk acoustic-optic modulators for beam deflection may utilize the acousto-optic effect for beam deflection. For example, surface acoustic waves (SAW) have been used to deflect the optical beam for optical switch application for many years. The beam deflection uses the concept of beam diffraction by the sound waves much as a diffraction grating does. To deflect the light beam into different angles, an aperiodic or chirp transducer 502 shown in FIG. 5 is used. Here the interdigitated spacing is gradually changed along the length of the transducer in the direction of propagation of the acoustic wave. This frequency-modulated surface produced by the multi-wavelength surface acoustic wave creates the beam deflection in this case in the horizontal direction. The basic construction of the system consists of an optical waveguide layer 504 which can be made of ZnO thin film formed in a Y-cut LiNbO$_3$ substrate. The acoustic transducer used in waveguide modulation consists of an interdigitated, multi-periodic pattern of metal fingers deposited directly onto the waveguide surface.

For the vertical beam deflection, a bulk acoustic-optic modulator 506 is used. The concept is similar to the SAW device where the Bragg-type diffraction took place due to the acousto-optic effect. In this embodiment, the multi-wavelength bulk acoustic wave generates a grating pattern that causes the incident optical beam to deflect in the direction perpendicular to the wave fronts. Thus, a raster light display is created when a light goes through these two acousto-optic mediums.

Figure 10:
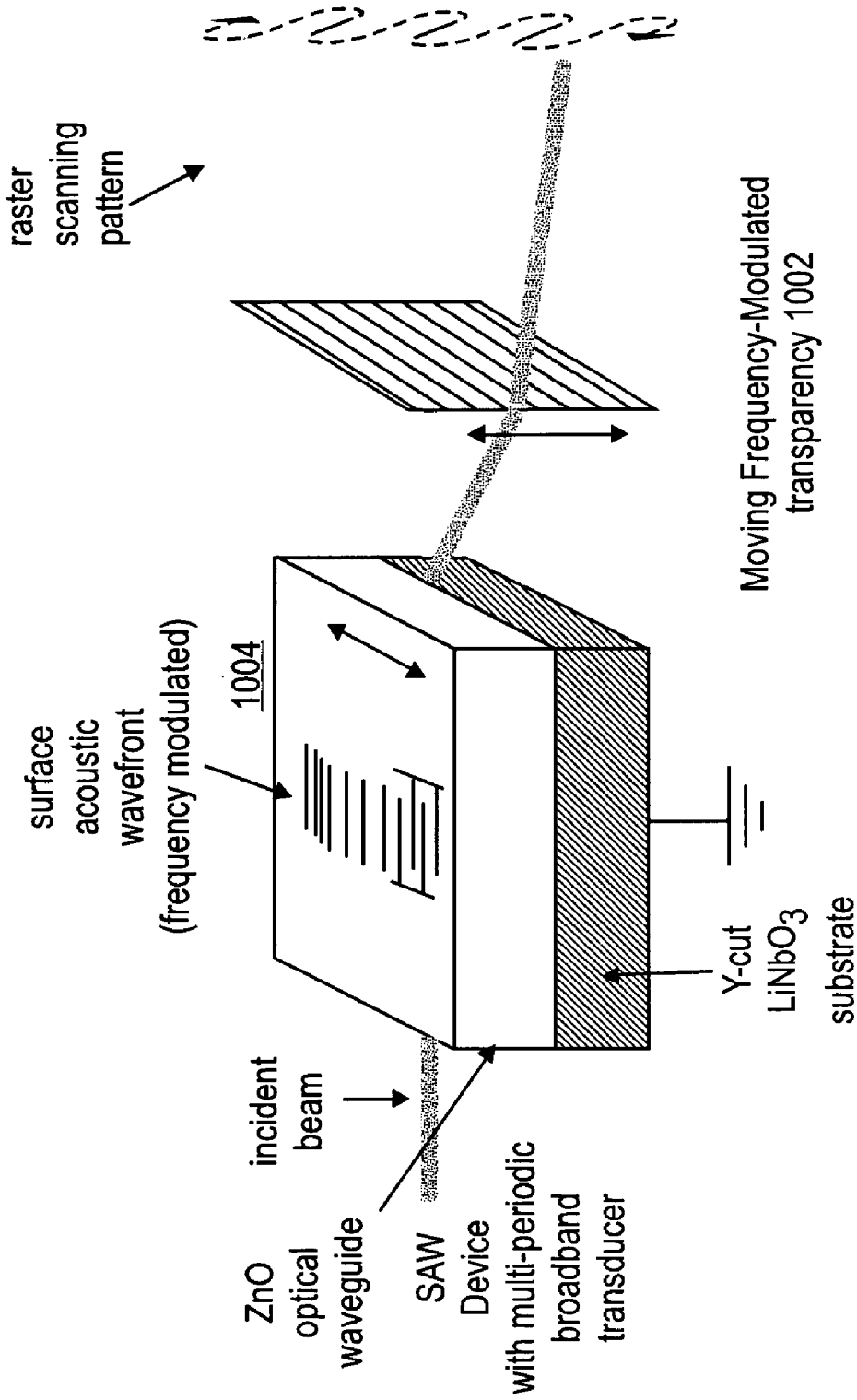
FIG. 10 is a perspective diagram illustrating a two-dimensional vertical beam deflection combined implementing a surface acoustic wave (SAW) device according to an embodiment of the present invention.

Alternative vertical beam deflection combine with SAW device to form a two dimensional beam deflection is shown in FIG. 10. In the illustrated embodiment, a frequency-modulated transparency 1002 instead of Acoustic-optic modulator is used for the vertical beam deflection. Two-dimensional beam steering is created by the optical frequency-modulated transparency 1002 for the vertical beam deflection and an acoustic SAW device 1004 for horizontal beam deflection.

Embodiments of the present invention also may be used in display systems. Many small-scale image display systems, such as head mounted displays (HMDs), beam light from an optical fiber onto deflectable mirrors or rotating polygonal mirrors to produce an image on an image plane. This approach also has many size limitations. For instance, light beams of less than 3 millimeter (mm) are impractical for displays using mirrors, because mirror scanners and grating deflectors must be significantly larger than the light beam diameter to avoid clipping the beam or adding diffraction. Reducing the diameter of a conventional display device reduces the possible number of pixels, and thus reduces the resolution and/or field of view (FOV) of the device. However, a reduction in diameter and size would enable construction of more comfortable HMDs, and enable integration of display with other functional devices.

Figure 6:
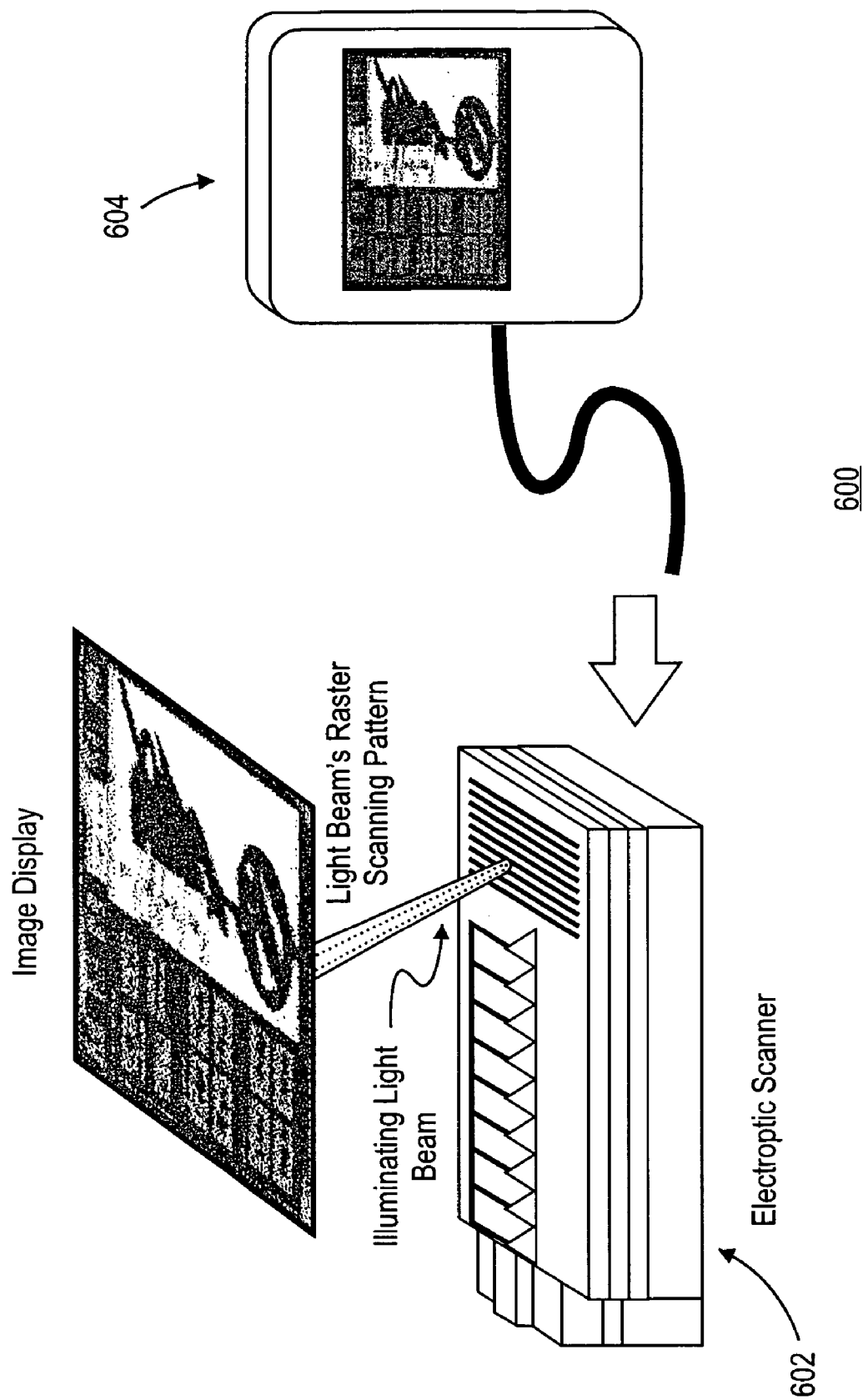
FIG. 6 is a high-level block diagram of a scanning display system according to an embodiment of the present invention.

The small size, high resolution display and ultra high speed electro-optic beam steering mechanism make this non-moving device an ideal choice for micro-display. A small, integrated display system such as the proposed scanning device will greatly improve mobility for a head mounted display and enable very localized display of images. High scanning speed (gigahertz range) increases spatial resolution (e.g. more lines per scan). SVGA image or greater resolution is easily obtained without increasing the overall design size. Despite its small size, the integrated system should still be capable of providing a great field of view, a good image size, and ultra high resolution. FIG. 6 illustrates a display system 600 using an electro-optic scanner 602 and a display 604 according to an embodiment of the present invention.

Potential applications of display systems implemented according to embodiments of the present invention may vary from the military, health, manufacturing, security, to a computer monitor and a high definition television.

As described above, embodiments of the present invention may be implemented using hardware, software, or a combination thereof. In implementations using software, the software may be stored on a machine-accessible medium. A machine-accessible medium includes any mechanism that may be adapted to store and/or transmit information in a form accessible by a machine (e.g., a computer, network device, personal digital assistant, manufacturing tool, any device with a set of one or more processors, etc.). For example, a machine-accessible medium includes recordable and non-recordable media (e.g., read only memory (ROM), random access memory (RAM), magnetic disk storage media, optical storage media, flash memory devices, etc.), as recess as electrical, optical, acoustic, or other form of propagated signals (e.g., carrier waves, infrared signals, digital signals, etc.).

In the above description, numerous specific details, such as, for example, particular processes, materials, devices, and so forth, are presented to provide a thorough understanding of embodiments of the invention. One skilled in the relevant art will recognize, however, that the embodiments of the present invention may be practiced without one or more of the specific details, or with other methods, components, etc. In other instances, structures or operations are not shown or described in detail to avoid obscuring the understanding of this description.

Reference throughout this specification to "one embodiment" or "an embodiment" means that a particular feature, structure, process, block, or characteristic described in connection with an embodiment is included in at least one embodiment of the present invention. Thus, the appearance of the phrases "in one embodiment" or "in an embodiment" in various places throughout this specification does not necessarily mean that the phrases all refer to the same embodiment. The particular features, structures, or characteristics may be combined in any suitable manner in one or more embodiments.

The terms used in the following claims should not be construed to limit embodiments of the invention to the specific embodiments disclosed in the specification and the claims. Rather, the scope of embodiments of the invention is to be determined entirely by the following claims, which are to be construed in accordance with established doctrines of claim interpretation.

What is claimed is:

1. A two-dimensional image scanner comprising:
a horizontal beam deflector disposed in a waveguide, the waveguide being an electro-optic polymer, the horizontal beam deflector to disperse an incident light beam into a spectrum in a horizontal direction;
a vertical beam deflector disposed in the waveguide and optically coupled to the horizontal beam deflector, the vertical beam deflector to deflect the horizontally dispersed spectrum in a vertical direction; and
means for applying an electrical charge to the electro-optic polymer,
wherein the horizontal beam deflector comprises at least one of a cascaded grism array, a cascaded convex prism array, and/or a cascaded concave prism array.

2. The scanner of claim 1, further comprising a light source integrated with the optical beam deflectors to provide illumination of a region of interest.

3. The scanner of claim 1, further comprising a photodetector to detect reflected intensity.

4. The scanner of claim 2, wherein the light source comprises at least one of an unpackaged laser diode or a pigtail laser diode.

5. The scanner of claim 2, wherein the light source is at least one of:
end-butted to the optical scanner; and
attached adjacent to the optical scanner using mechanical fiber coupler.

6. The scanner of claim 2, wherein the light source comprises:
a broadband light emitting diode source; and
a tunable color filter to provide a color spectrum of light the tunable color filter comprising at least one of:
an optical resonant cavity;
a grating; and
a prism.

7. The scanner of claim 2, wherein an output of a first individual grism in a cascaded grism array is optically coupled to an input of a next individual grism in the cascaded grism array.

8. The scanner of claim 3, wherein an output of a last individual grism in a cascaded grism array is coupled to an input of the vertical beam deflector.

9. The scanner of claim 1, wherein the horizontal beam deflector comprises a cascaded right angle prism array.

10. The scanner of claim 1, wherein the vertical beam deflector comprises a Bragg grating coupler.

11. The scanner of claim 1, wherein the electro-optic polymer is to change index of refraction in response to an applied electrical charge.

12. The scanner of claim 1, wherein the electro-optic polymer is operationally coupled to:
a prism array, the prism array comprising a grism array, a right angle prism array, a convex prism array, or a concave prism array; and
a Bragg grating coupler.

13. The scanner of claim 1, further comprising a light source coupled to an input of the horizontal beam deflector.

14. A method for acquiring a two-dimensional display, comprising:
passing a light beam through a horizontal beam deflector disposed in a waveguide made from an electro-optic polymer;
dispersing the light beam into a spectrum in a first direction as the light beam passes through the horizontal beam deflector, wherein light in the spectrum includes several wavelengths;
passing light in the spectrum through a Bragg grating coupler disposed in the waveguide, the Bragg grating coupler having a Bragg wavelength;
deflecting the light in the spectrum having the Bragg wavelength in a second direction orthogonal to the first direction;
applying a varying electrical charge to the waveguide to change the Bragg wavelength of the Bragg grating coupler.

15. The method of claim 14, further comprising:
detecting reflected intensity using an array of built-in photodetectors; and
reconstructing the image using the detected signals.

16. The method of claim 15, further comprising generating the light beam using a light source.

17. The method of claim 15, further comprising an array of photon detectors detecting the emitted light that is reflected from a target.

18. The method of claim 15, further comprising detecting the light having the Bragg wavelength.

19. The method of claim 15, wherein the light source comprises a plurality of color elements, each of the plurality of color elements producing a different color light.

20. The scanner of claim 1, wherein the scanner has at least two dimensions smaller than one millimeter.

21. The method of claim 15, further comprising a controller that causes an input voltage supply to drive the horizontal and vertical beam deflectors in a pattern relative to a target to do at least one of:
display an image on the target; and
acquire an image of the target.

22. The method of claim 14, wherein beam deflections move in a limited region of interest to scan light onto an image plane to create an image.

23. A scanner, comprising:
a horizontal beam deflector disposed in a waveguide, the waveguide including an electro-optic polymer, the horizontal beam deflector to disperse an incident light beam into a spectrum in a horizontal direction;
a vertical beam deflector disposed in the waveguide and optically coupled to the horizontal beam deflector, the vertical beam deflector to deflect the horizontally dispersed spectrum in a vertical direction;
means for applying an electrical charge to the electro-optic polymer; and
an integrated detector array coupled to an output of the vertical beam deflector.

24. The scanner of claim 23, wherein the horizontal beam deflector includes an array of prisms, each prism having at least one shaped electrode to induce a variation in index of refraction in the electro-optic polymer, wherein the variation in index of refraction is to cause light propagating in the horizontal beam deflector to deviate from its original path in an interface between each prism and air.

25. The scanner of claim 23, wherein the horizontal beam deflector and/or the vertical beam deflector includes an aperiodic transducer disposed on the electro-optic polymer.

26. The scanner of claim 23, wherein the horizontal beam deflector and/or the vertical beam deflector includes an acousto-optic transducer disposed on the electro-optic polymer.

* * * * *

UNITED STATES PATENT AND TRADEMARK OFFICE
CERTIFICATE OF CORRECTION

PATENT NO. : 7,233,710 B2  Page 1 of 1
APPLICATION NO. : 11/068939
DATED : June 19, 2007
INVENTOR(S) : Wang et al.

It is certified that error appears in the above-identified patent and that said Letters Patent is hereby corrected as shown below:

In column 1, at line 10, insert --This invention was made with US Government support under grant number R21 EB004564 awarded by the National Institutes of Health. The US Government has certain rights in this invention.--.
In column 9, at line 54, delete "☐m" and insert --µm--.

Signed and Sealed this

Eleventh Day of December, 2007

JON W. DUDAS
*Director of the United States Patent and Trademark Office*